US005603332A

United States Patent [19]

O'Connor

[11] Patent Number: 5,603,332
[45] Date of Patent: Feb. 18, 1997

[54] METHOD AND APPARATUS FOR MONITORING THE SYSTEMIC ABSORPTION OF IRRIGATION FLUID DURING OPERATIVE HYSTEROSCOPY

[75] Inventor: Terence M. O'Connor, Dallas, Tex.

[73] Assignee: Technological Services, Inc., Dallas, Tex.

[21] Appl. No.: 378,803

[22] Filed: Jan. 27, 1995

[51] Int. Cl.⁶ .......................... A61M 15/08; G01N 31/00
[52] U.S. Cl. .............................. 128/716; 128/719
[58] Field of Search .................... 128/716, 719, 128/730

[56] References Cited

U.S. PATENT DOCUMENTS

| | | | |
|---|---|---|---|
| 2,795,223 | 6/1957 | Stampe. | |
| 3,661,528 | 5/1972 | Falk. | |
| 3,817,238 | 6/1974 | Matson | 128/716 |
| 4,297,871 | 11/1981 | Wright et al. | |
| 4,509,359 | 4/1985 | Gedeon et al. | 128/719 |
| 4,656,008 | 4/1987 | Gump | 128/719 |
| 4,736,619 | 4/1988 | Legrand. | |
| 4,756,670 | 7/1988 | Arai | 128/719 |
| 5,046,491 | 9/1991 | Derrick | 128/716 |

OTHER PUBLICATIONS

Fleisher, "Hyponatremia and possible Uterine Perforation During Endometrial Rollerball Ablation", *Anesth. Analg.* vol. 77, pp. 860–861, USA, (1993).

D'Agosto, "Absorption of Irrigating Solution during Hysteroscoic Metroplasty". *Anestheology*, vol. 72, vol. 72, pp. 379–380, U.S.A., (1990).

Endometrial Ablation Complicated by Fatal Hyponatremia Encophalopathy, *J. Am. Med. Assn.*, vol. 270, No. 10, pp. 1230–1232, U.S.A. (1993) by Arieff.

O'Connor, "Hyponatremia Encephalopathy After Endometrial Ablation", *J. Am. Med. Assn.* vol. 271, No. 5, pp. 343–344 (1994).

Krohn, "Dilutional Hypocalcemia in Association with Dilutional Hyponatremia", *Anestheology*, vol. 79, No. 5 (1993), U.S.A.

Hahn, "Immediate Detection of Irrigant Absorption During Transurethral Resection of the Prostate", *Can. J. Anesth.* vol. 36, No. 1, pp. 86–88 (1989), Canada.

(List continued on next page.)

Primary Examiner—Angela D. Sykes
Assistant Examiner—Stephen Huang
Attorney, Agent, or Firm—Thomas V. Malorzo

[57] ABSTRACT

A ported connecting tube is interposed between the gas delivery hose of an anesthesia gas delivery machine and the outlet of an endotracheal tube. One end of a flexible conduit is inserted into the port in the connecting tube and the other end is connected to a breath alcohol meter thereby placing the sampling chamber of the meter in flow registration with the endotracheal tube. During operative hysteroscopy, a refrigerated solution containing, optimally 1% Ethanol is used to irrigate the surgery site, and the patient's expired breath is periodically sampled to determine the presence and quantity of ethanol therein. The presence of ethanol indicates systemic absorption of the irrigation fluid by the patient, which absorption may cause undesirable operative and post operative complications in the patient.

11 Claims, 4 Drawing Sheets

OTHER PUBLICATIONS

Hulten, "Monitoring Irrigating Fluid Absorption During Transurethral Resection of the Prostate (TURP), A Comparison of 1% and 2% Ethanol as a Tracer" *Scand. J. Urol. Nephrol*, vol. 23, pp. 103–108 (1988), Sweden.

Hahn, "Prevention of TUR Syndrome by Detection of Trace Ethanol in Expired Breath", *Anesthesia*, vol. 45, No. 7, (1990)Pub. unknown.

Hahn, "Calculation of Irrigant Absorption by Measurement of Breath Alcohol Level during Transurethral Resection of the Prostate" *British J. of Urology*, vol. 68, pp. 390–393 (1991), G. B.

Hahn, Monitoring TURP with Ethanol, *The Lancet*, vol. 338 p. 1802, Dec. 21, 1991, G. B.

Note: Monitoring TURP, *The Lancet*, vol. 338, pp. 606–607 Sep. 7, 1991, G. B.

Hjertberg, "Use of Ethanol as Maker Substance To Increase Patient Safety During Transurethral Prostatic Resection", Urology, vol. 38, No. 5, pp. 423–428 (1991) U.S.A.

Hulten, "Monitoring of Irrigating Fluid Adsorption During Transurethral Prostatectomy", Anaesthesia, vol. 46, pp. 349–353 (1991) Country, Unk.

O'Connor, "Use of Ethanol – Marked Irrigation Fluid for Operative Hysteroscopy" Society for Ambulatory Anesthesia Apr. 29, 1994, U.S.A.

"Ethanol as a Marker Shows Pulmonary Edema During Hysteroscopy", *Anestheology News*, Jul. 1994, pp. 1 and ? U.S.A.

Product Data Sheet: Narkomed 2B, Pub. No. PL000001–001 North American Drager, Pub. Date Unk., U.S.A.

Summary of Patient Data

| # | Patient Wt. (lbs) | Scope Time (mins) | Sorbitol In (cc) | Sorbitol Out (cc) | IV Fluids (cc) | Peak EtOH (g/100 ml) | Pitres-sen |
|---|---|---|---|---|---|---|---|
| 1 | 204 | 23 | 5000 | 3700 |  | .001 | no |
| 2 | 126 | 21 | 9000 | 8400 | 900 | .019 | yes |
| 3 | 142 | 25 | 6400 | 6300 | 1400 | 0 | no |
| 4 | 197 | 30 | 4000 | 4000 |  | 0 | yes |
| 5 | 116 | 63 | 10900 | 11300 | 2000 | 0 | no |
| 6 | 112 | 45 | 20500 | 21600 | 800 | 0 | yes |
| 7 | 160 | 21 | 4500 | 4500 | 700 | 0 | no |
| 8 | 145 | 78 | 9700 | 8600 | 1400 | .001 | yes |
| 9 | 155 | 46 | 10900 | 9200 | 1100 | 0 | yes |
| 10 | 135 | 33 | 5100 | 4900 | 800 | 0 | yes |
| 11 | 130 | 43 | 8600 | 8300 | 1300 | .007 | yes |
| 12 | 121 | 36 | 5500 | 5100 |  | .014 | yes |
| 13 | 280 | 32 | 3500 | 4200 | 800 | 0 | no |
| 14 | 112 | 30 | 9000 | 9200 | 900 | .005 | yes |
| 15 | 147 | 42 | 3800 | 3800 | 900 | .005 | yes |
| 16 | 120 | 20 | 5800 | 6000 | 700 | .004 | yes |
| 17 | 124 | 38 | 6000 | 6300 |  | 0 | yes |
| 18 | 130 | 55 | 6000 | 6000 | 1100 | 0 | yes |
| 19 | 224 | 59 | 11400 | 11700 | 800 | .001 | yes |

Fig. 4

METHOD AND APPARATUS FOR MONITORING THE SYSTEMIC ABSORPTION OF IRRIGATION FLUID DURING OPERATIVE HYSTEROSCOPY

FIELD OF THE INVENTION

This invention relates to a method and apparatus for the monitoring of systemic absorption of irrigation fluids during surgery. More particularly, the invention is directed towards the use of an irrigation fluid which has been spiked with ethanol and the detection and measurement of tidal breath alcohol in patients undergoing operative hysteroscopy as a means of determining the occurrence of systemic absorption of irrigation fluids.

BACKGROUND OF THE INVENTION

As Operative Hysteroscopy has gained popularity as a method to treat problems which formerly would have required open abdominal surgery, a number of complications of water and electrolyte imbalance secondary to the absorption of the irrigation fluid used during the procedure have become recognized.[1-5].

In open abdominal surgery, when irrigation fluids are instilled onto the surgical site, they are typically recovered using a suction apparatus in conjunction with a graduated collection bottle so that the surgeon has a reasonable estimate of the amount of fluid instilled, the amount recovered by suction, and, therefore, the amount of irrigation fluid available for systemic absorption.

In contrast, however, operative hysteroscopy generally requires injection of irrigation fluids under pressure to distend the uterus and because a relatively small opening is utilized during the surgery, the irrigation fluid is recovered as outflow. Because of the necessity of using this method of recovery, the collection and measurement of irritation fluids so injected is inaccurate with some irrigation fluid frequently being lost by absorption into the various drapes and bed linens as well as through spillage. In addition, the instilled irrigation fluid may be admixed with body fluids thereby adding to the apparent volume of outflow fluid. Thus the surgeon frequently has to guess whether or not, and if so, how much fluid is available for systemic absorption by the patient.

Irrigation fluids typically employed in operative hysteroscopy include, by example and not by way of limitation, 3% Sorbitol, Hyscon (comprising 32% Dextran 70 in water) and Saline.

Irrigation fluids are typically refrigerated and administered cold in an attempt to control bleeding.

Apparatus for sampling expired air are well known. Examples of such apparatus are shown in U.S. Pat. No. 2,795,223 to Stampe, U.S. Pat. No. 3,661,528 to Falk, and U.S. Pat. No. 4,297,871 to Wright, et al. Similarly, devices for measuring the alcohol content in exhaled breath, such as that shown in U.S. Pat. No. 4,736,619 to Legrand are also well known.

Similarly, the measurement of tidal alcohol in patients undergoing Transurethral Prostatectomy (TURP) to avoid many of the same complications as has been recognized in Hysteroscopy patients has also been documented.[6-13] Where tidal alcohol has been used as a measurement or indicator of the absorption of irrigation fluid, from 1% to 2% Ethanol by volume is added to the irrigation fluid before it is instilled in the patient.

However, Operative Hysteroscopy is fundamentally different from TURP in that higher injection pressures, on the order of 60–80 mm. Hg are used, and, unlike the TURP patient, if the Hysteroscopy patient has patent fallopian tubes, there is a direct pathway into the peritoneal cavity. In addition, whereas TURP is frequently performed using local anesthesia, such as epidural or spinal anesthesia, Hysteroscopy is frequently performed with the patient "asleep" under general anesthesia.

Accordingly there is need for a means for the detection and measurement of end tidal alcohol in patients who are under general anesthesia to determine the occurrence of the absorption of irrigation fluids.

THE INVENTION

Objects

It is therefore an object of this invention to provide an apparatus which can detect and measure end tidal alcohol in the breath of an anesthetized patient.

It is a further object of this invention to provide an apparatus which can detect and measure end tidal alcohol in the breath of a patient under general anesthesia.

It is another object of this invention to provide a method by which the apparatus described herein can be used to predict the systemic absorption of irrigation fluid at a surgical site A still further object of this invention is to provide an apparatus which can detect and measure end tidal alcohol in the breath of an anesthetized patient undergoing Operative Hysteroscopy.

A still further object of this invention is to provide a method whereby the presence of end tidal alcohol in the breath of an anesthesized patient may be used as an indicator of the absorption of irrigation fluid during surgery.

Another and still further object of this invention is to provide a method whereby the presence of end tidal alcohol in the breath of an anesthesized patient may be used as an indicator of the absorption of irrigation fluid during operative hysteroscopy.

The novel features of this invention are set forth with particularity in the claims. The invention will be best understood from the following description when read in conjunction with the accompanying drawings and figures.

BRIEF DESCRIPTION OF THE DRAWINGS AND FIGURES

FIG. 4 is a tabular summary of patient data.

DETAILED DESCRIPTION OF THE INVENTION

Figure 1:
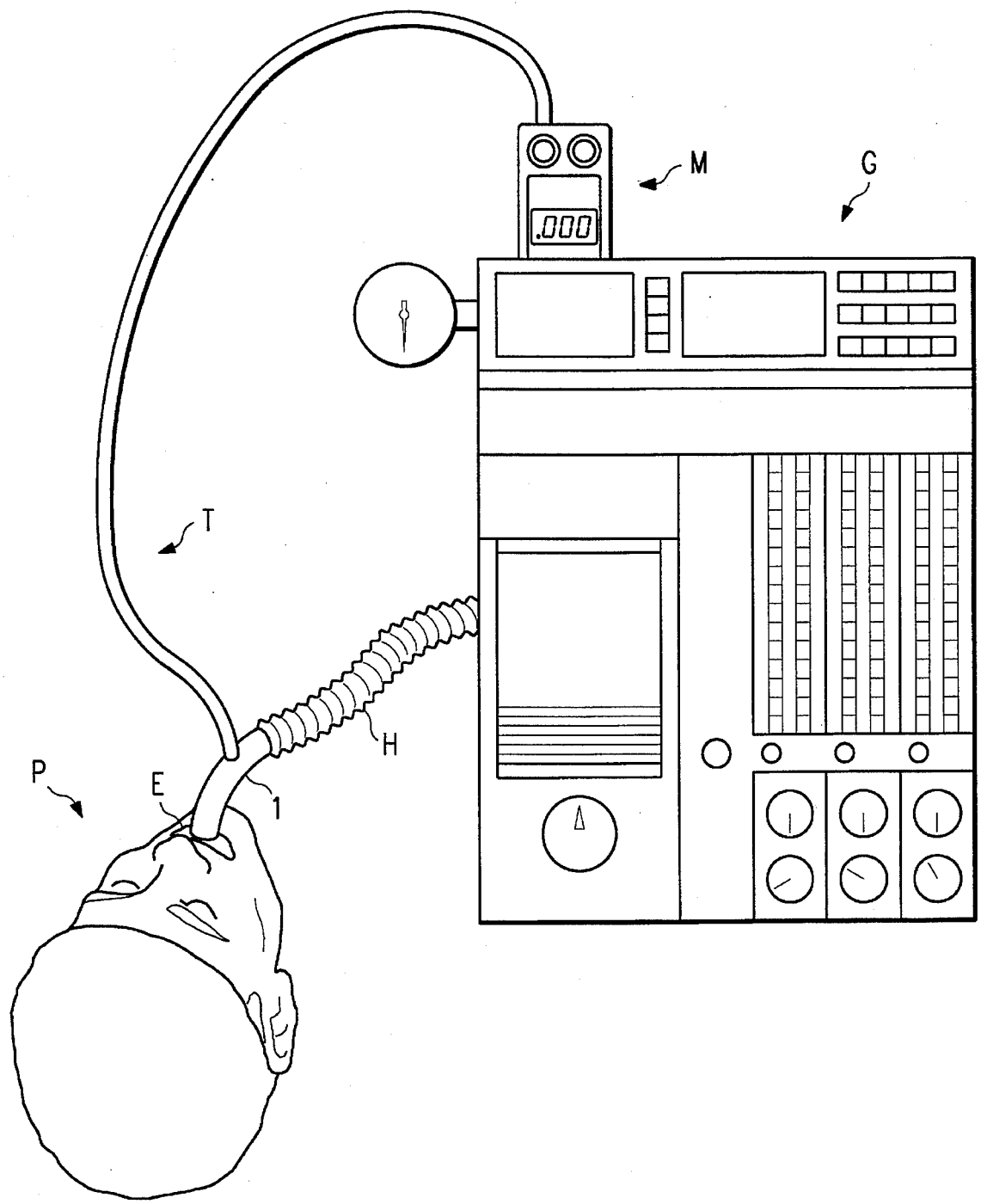
FIG. 1 is a schematic view of an anesthesia gas delivery device and a breath alcohol measurement device connected to a patient under general anesthesia.

In the description that follows, like parts are marked throughout the specification and drawings with the same reference numerals, respectively. The drawings are not necessarily to scale and the proportions of certain parts have been exaggerated to better illustrate the details of the present invention.

Referring now to FIG. 1, Patient P has been incubated with an endotracheal tube, E, of a type commonly known in the art. Ported connecting tube 1 is connected in flow registration between endotrachial tube T and flexible gas delivery hose H. Gas delivery hose H is in turn connected in flow registration to the gas outlet port (not shown) of an anesthesia gas delivery device, G, of a type commonly known in the art, such as the Narkomed 2B™ produced by North American Dräger of Telford, Pa. Such anesthesia gas delivery machines commonly contain several precision flow meters and metering valves, as well as a bellows type ventilator, canisters of absorbent and patient monitoring apparatus such as blood gas measurement devices and electrocardiogram equipment. Such anesthesia gas machines are designed to be placed intermediate a high pressure source of anesthesia gas and the patient.

Set atop gas delivery device G is a "sniffer-type" breath alcohol vapor concentration measuring device, or meter, M, of a kind commonly known in the art, such as the Alco-Sensor III™ produced by Intoximeters, Inc., St. Louis, Mo. Such sniffer type meters commonly have an internal vacuum producing bellows which, when manually activated, draws a small portion of the exhaled air into the sampling chamber of the device. Except by means of flexible tube T, described below, there is no physical connection between the gas delivery device, G, and the alcohol meter, M, with the device G merely serving as a pedestal or platform upon which meter M is placed.

Meter M is connected to ported connecting tube 1 by means of a flexible tube T in flow registration between the port in connecting tube 1, as described in further detail below, and the sampling inlet of meter M.

Figure 2:
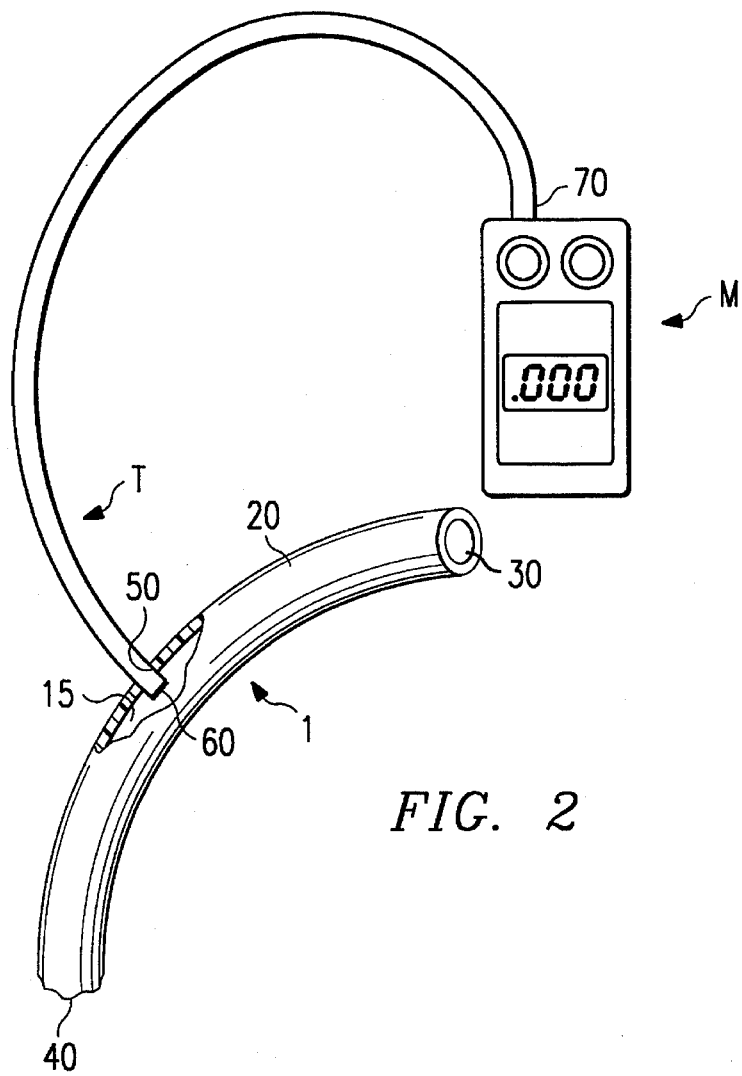
FIG. 2 is a plan view in partial cross section of the apparatus and its connection to a tidal alcohol measurement device.

Referring now to FIG. 2, ported connecting tube 1 comprises a tube having an interior surface 10 and an exterior surface 20. Said interior surface forms the outer boundary of fluid passage 15. A first opening 30 and a second opening 40 in flow registration with each other and form the ends of said passage 15. Intermediate said first opening 30 and said second opening 40 is flow port 50 which connects said interior surface 10 and said exterior surface 20 thereby forming a flow passage between passage 15 and the exterior of tube 1.

Flow port 50 is sized so that flexible tube T may be inserted therein and its diameter is such that tube T is held in place by a friction fit.

Flexible tube T has a first opening 60 in flow registration with a second opening 70. Second opening 70 is fitted to and in flow registration with Breath Alcohol Meter M, and first opening 60 is in flow registration with passage 15.

Exterior surface 20, proximate first opening 30, is formed to be firmly attached to flexible Gas Delivery Hose H. Proximate to second opening 40, exterior surface 20 is formed to be firmly attached to endotrachial tube T so that passage 15 is in flow registration with the Gas Delivery Hose H and the endotrachial tube T.

Figure 3:
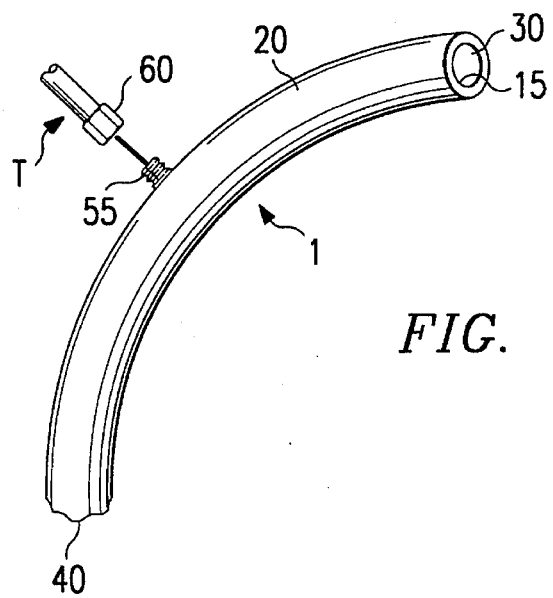
FIG. 3 is a plan view of an alternative embodiment of the invention.

Turning now to FIG. 3, in an alternative embodiment, rather than retaining tube T in flow port 50 by means of a friction fit, a connector means 55 having a flow passage therethrough (not shown), shown here by way of an example and not by means of limitation as a screw type fitting, is molded as a part of exterior surface 20. A mating fitting 60 is made up on the end of tube T thereby providing a more secure threaded attachment and therefore providing a more secure flow passage between passage 15 of the ported connecting tube 1 and breath alcohol meter M.

EXAMPLES

Referring now to FIG. 4, results are shown for nineteen (19) patients who have undergone Operative Hysteroscopy.

An AlcoSensor III™ breath alcohol measurement system, sold by Intoximeters, Inc. was attached to the anesthesia circuit as described above and as shown in FIGS. 1 and 2 was standardized according to the supplier's directions.

The patient was incubated with a cuffed endotracheal tube T of a type commonly known in the art. The endotracheal tube T was connected in flow registration with ported connecting tube T, which, in turn, was connected in flow registration with gas delivery hose H. The gas delivery hose H was then connected in flow registration with gas delivery device G.

After the patient was anesthesized with a gaseous general anesthesia agent and surgery had commenced, and irrigation of the surgical site was required, a solution of 1% Ethanol in 3% Sorbitol was used. Once irrigation was commenced, breath alcohol concentration measurements in the end-tidal air of the patient were taken every five (5) minutes to determine if any of the irrigation fluid was being systemically absorbed.

RESULTS

FIG. 4 sets out the patient weight in lbs.; the Scope time, which is the surgery time in minutes; Sorbitol In and Sorbitol Out, is the number of cc's of the irrigation fluid instilled and recovered on outflow, respectively; IV Fluids is the number of cc's of fluid administered intravenously to the patient; Peak EtOH is the maximum quantity of ethanol (expressed as g/100 ml) detected in the patient's expired breath during the surgery; and Pitressen which refers to whether or not the drug Pitressen, also known as vasopressen was administered during the surgery.

A comparison of the columns in FIG. 4 labeled "Sorbitol In" and "Sorbitol Out" shows a discrepancy between irrigant instillation and outflow varied from a loss of 1700 cubic centimeters (cc's) to a net gain of 1100 cc's. This variation illustrates the unreliability of the outflow measurement method as described above.

In the nineteen patients documented in FIG. 4, end—tidal air containing greater than 0.001 g/100 ml EtOH was documented in nine patients. In five patients, the amount of "Sorbitol In" was greater than the amount of Sorbitol recovered (Sorbitol Out) indicating systemic absorption of Sorbitol by the patient at the surgical site. In four patients, the amount of "Sorbitol Out" exceeded the amount of Sorbitol instilled (Sorbitol In) indicating the inclusion of blood or other bodily fluid in the Sorbitol removed from the patient.

Patient 1 had a previously unrecognized uterine peroration which was identified after the surgery commenced. She showed a rapid apparent loss of Sorbitol, but no appreciable level of Ethanol in her expired air. Surgery was rapidly completed with intermittent irrigation.

Figure 5:
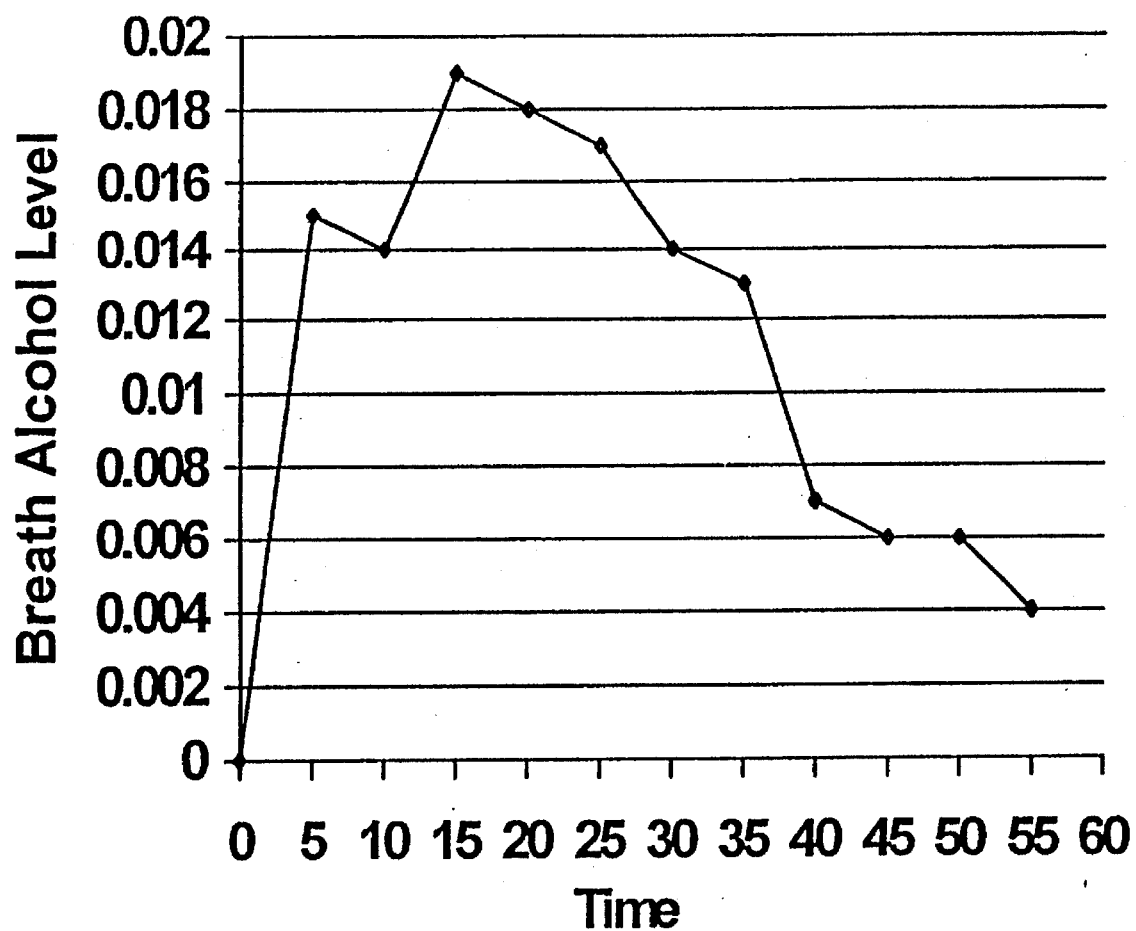
FIG. 5 is a graphical presentation of Breath Alcohol Level as a function of time.

Referring now to FIG. 5, patient No. 12 showed a breath alcohol level of 0.019 g/100 ml expired air within ten minutes into the procedure. Hahn[10] has shown that a level of 0.025 gm/100 ml corresponds to approximately one liter of systemic absorption of irrigation fluid and probably represents a critical warning level. Thus the procedure was quickly terminated and the patient taken to recovery. Using the outflow method, an estimated 600 ml of irrigation fluid was lost, but due to the inaccuracy of this method, the amount of fluid lost must be considered suspect.

This invention has been described with reference to an exemplary embodiment, however, the foregoing description is not intended to be construed in a limiting sense. Various modifications of the disclosed embodiment as well as alternative applications of the invention will be suggested to persons skilled in the art by the foregoing specification and illustrations. It is therefore contemplated that the appended claims will cover any such modifications, applications or embodiments as fall within the true scope of the invention.

REFERENCES

1. Keith Fleisher, M.D., et al, "Hyponatremia and Possible Uterine Peforation During Endometrial Rollerball Ablation, *Anesth. Analg.*, Vol 77, pp. 860–61 (1993).
2. Joseph D'Agosto, M.D., et al, "Absorption of Irrigating Solution during Hysteroscopic Metroplasty, *Anestheology*, Vol 72, pp. 379–80 (1990).
3. Allen I. Arieff, M.D., et al, "Endometrial Ablation Complicated by Fatal Hyponatremic Encephaolpathy, *J. Am. Med. Assn.*, Vol. 270, No. 10, pp 1230–32 (1993).
4. Letters: "Hyponatremic Encephalopathy After Endometrial Ablation", *J. Am. Med. Assn.*, Vol. 271, No. 5, pp. 343–44 (1994).
5. Jonathan S. Krohn, M.D., "Dilutional Hypocalcemia in Association with Dilutional Hyponatremia", *Anestheology*, Vol. 79., No. 5 (1993).
6. Robert Hahn. M.D., et al., "Immediate detection of irrigant absorption during transurethral prostatectomy: case report", *Can. J. Anaesth.*, Vol. 36, No. 1, pp 86–8 (1989).
7. Jan O. Hulten, et al., "Monitoring Irrigating Fluid Absorption During Transurethral Resection of the Prostate (TURP); A Comparison Between 1% and 2% Ethanol As A Tracer, *Scand. J. Urol. Nephrol.* Vol. 23. pp. 103–08 (1988).
8. R. G. Hahn, M.D., "Prevention of TUR syndrome by detection of trace ethanol in expired breath", *Anaesthesia*, Vol. 45, No. 7, pp. 577–81 (1990).
9. R. G. Hahn, "Calculation of Irrigant Absorption by Measurement of Breath Alcohol Level during Transurethral Resection of the Prostate", *British Journal of Urology*, Vol. 68, pp. 390–93 (1991).
10. R. G. Hahn, "Monitoring TURP with ethanol", *The Lancet*, Vol. 338, p. 1602, (Dec. 21, 1991).
11. Note: "Monitoring TURP", *The Lancet*, Vol. 338, pp. 606–7, (Sep. 7, 1991).
12. Hans Hjertberg, M.D., et al, "Use of Ethanol as Marker Substance To Increase Patient Safety During Transurethral Prostatic Resection", *Urology*, Vol. 38, No. 5, pp 423–8 (1991).
13. J. Hultén, et al., "Monitoring of irrigating fluid adsorption during transurethral prostatectomy", *Anaesthesia*, Vol. 46, pp. 349–53, (1991).
14. Terence M. O'Connor, M.D., "Use of Ethanol—Marked Irrigation Fluid for Operative Hysteroscopy", presented at 1994 Annual Meeting, Society for Ambulatory Anesthesia, Apr. 29, 1994.
15. "Ethanol as a Marker Shows Pulmonary Edema During Hysteroscopy", *Anestheology News.*, July, 1994 at 1.

What I claim as my invention is:

1. An apparatus for determining if irrigation fluid is being systemically absorbed by a patient undergoing operative hysteroscopy comprising a tubular connector having a flow passage therethrough and a first opening connected to a second opening by means of said flow passage, said first opening connected in flow registration with a cuffed endotracheal tube, said second opening connected in flow registration with a flexible gas delivery hose of an anesthesia gas mixing and metering device, said tubular connector having a port intermediate said first opening and said second opening providing fluid passage between interior and exterior of said tubular connector, a flexible tube with a fluid bore extending the length of said flexible tube with a first opening in flow registration with said fluid bore located at a first end of said tube, said first end being retained by retaining means so that said first opening is retained in fluid communication with said port in said tubular connector, and a second opening in flow registration with said fluid bore located at a second end of said tube, said second end being attached to a sampling inlet of a manually activated alcohol vapor concentration measuring device so that the second opening is in fluid communication with said sampling inlet, said retaining means comprising a port in said connector with a diameter slightly smaller than outside diameter of said flexible tube such that the first end of said tube is retained within said port in said tubular connector by means of a friction fit.

2. The Apparatus described in claim 1 wherein said means for retaining said tube in fluid communication with the fluid passage of said connector comprises connector means having a first part fixedly attached to said connector and a second part fixedly attached to said tube, said first part and said second part being releasably joinable to each other thereby forming a leak proof seal therebetween to provide an integral flow conduit between said connector and said inlet of said alcohol measuring device.

3. The method of determining if irrigating fluid is being systemically absorbed by a patient during an operative hysteroscopy procedure comprising the steps of:
   a. intubating the patient with an endotracheal tube;
   b. generally anesthetizing the patient with gaseous anesthesia;
   c. using irrigating fluid to which ethanol has been added to irrigate the hysteroscopy site; and
   d. periodically sampling the patient's exhaled breath to determine concentration of ethanol therein.

4. The method of determining if irrigating fluid is being systemically absorbed set forth in claim 3 wherein the irrigating fluid is chosen from the group consisting of 3% Sorbitol (aqueous), Hyscon, and saline.

5. The method of determining if irrigating fluid is being systemically absorbed set forth in claim 3 wherein the irrigating fluid is 3% (Sorbitol (aqueous).

6. The method of determining if irrigating fluid is being systemically absorbed set forth in claim 5 wherein the irrigating fluid contains 1.0 percent Ethanol.

7. The method of determining if irrigating fluid is being systemically absorbed set forth in claim 3 wherein the irrigating fluid contains from 0.1 percent to 2.0 percent Ethanol.

8. The method of determining if irrigating fluid is being systemically absorbed during operative hysteroscopy wherein the improvement consists of:

using an irrigation fluid to which ethanol has been added; and periodically measuring the concentration of ethanol present in the end-tidal air of the patient.

9. The method of determining if irrigating fluid is being systemically absorbed fluid during operative hysteroscopy set forth in claim 8 wherein the irrigation fluid is chosen from the group consisting of 3% Sorbitol (aqueous), Hyscon, and saline.

10. The method of determining if irrigating fluid is being systemically absorbed during operative hysteroscopy set forth in claim 8 wherein from 0.1 to 2.0 percent ethanol is added to the irrigation fluid prior to instillation.

11. The method of determining the systemic absorption of irrigating fluid during operative hysteroscopy set forth in claim 10 wherein 1.0% ethanol is added to the irrigation fluid prior to instillation.

* * * * *